(12) United States Patent  (10) Patent No.: US 6,595,775 B1
Berk et al.  (45) Date of Patent: Jul. 22, 2003

(54) DENTAL MIRROR

(75) Inventors: Kenneth J. Berk, Newton, MA (US); Fredrick M. Berk, Brookline, MA (US); Donald Berk, Newton, MA (US)

(73) Assignee: Pulpdent Corporation, Watertown, MA (US)

( * ) Notice: Subject to any disclaimer, the term of this patent is extended or adjusted under 35 U.S.C. 154(b) by 0 days.

(21) Appl. No.: 09/663,903

(22) Filed: Sep. 18, 2000

(51) Int. Cl.7 ................................................. A61B 1/24
(52) U.S. Cl. ......................................................... 433/30
(58) Field of Search ..................... 433/30, 31; D24/139; 600/247, 248; 359/882

(56) References Cited

U.S. PATENT DOCUMENTS

| 548,817 | A |   | 5/1895 | McNaughton |         |
|---------|---|---|--------|------------|---------|
| 539,076 | A |   | 10/1895| Platt      |         |
| 1,844,733 | A | * | 2/1932 | Wise ........................... | 600/247 |
| 2,635,597 | A |   | 9/1953 | Canan      |         |
| 3,512,259 | A | * | 5/1970 | Gordon et al. ................ | 433/30  |
| 3,711,176 | A |   | 1/1973 | Alfrey, Jr.|         |
| 3,829,199 | A |   | 8/1974 | Brown      |         |
| 4,512,635 | A |   | 4/1985 | Melde      |         |
| D281,718 | S |   | 12/1985| Holstad    |         |
| 5,052,925 | A |   | 10/1991| Stalcup    |         |
| D329,899 | S |   | 9/1992 | Rihani     |         |
| 5,295,826 | A | * | 3/1994 | Yandell et al. ................ | 433/30  |
| D348,515 | S |   | 7/1994 | Mangione   |         |
| 5,655,904 | A |   | 8/1997 | Usui       |         |
| 5,906,487 | A | * | 5/1999 | Carr ........................... | 433/30  |
| 6,142,777 | A |   | 11/2000| Winston    |         |

OTHER PUBLICATIONS

Page 10 of a catalog of Hager Worldwide, Inc, Odessa Florida, date unknown.
Photo reproduction of prior art mirror of unknown origin, 3 pages with top side and rear views.

* cited by examiner

*Primary Examiner*—Cary E. O'Connor
(74) *Attorney, Agent, or Firm*—Lee & Hollander

(57) ABSTRACT

A dental mirror configured so that it is easier and more comfortable to manipulate than prior art mirrors. The dental mirror includes a handle which is attached to the mirror section with an s-shaped gooseneck so that the handle is offset upwardly. Additionally, grooves on the bottom and a finger rest on top at the distal end of the handle may be provided to further enhance it manipulatability.

21 Claims, 1 Drawing Sheet

DENTAL MIRROR

FIELD OF THE INVENTION

This invention is related to small, inexpensive mirrors suitable for use in dentistry.

BACKGROUND OF THE INVENTION

Dentists have long used small, handheld mirrors when performing dental procedures such as oral surgery and restorative dentistry. The stereotypical dental mirror has a stainless handle with a reflecting surface affixed at an angle on the end of the handle. The reflecting surface in such a dental mirror is usually provided by a conventional glass mirror.

Such dental mirrors have disadvantages. They are costly to manufacture. They have a high tendency to fog up due to the relatively large heat capacity and conductance of the glass and metal materials. This type of dental mirror also requires sterilization between patients via chemical or thermal processes.

Additionally, although the material in these dental mirrors can withstand chemical and thermal sterilization, the interface between the glass reflective surface and the metal handle is susceptible to retaining germs which may occasionally survive the sterilization process. Even when sterilization of the mirror is successful, unsightly debris and grit may be trapped in the gap around the glass mirror, and can be difficult to remove.

The cost of dental mirrors becomes an important factor with a new dental technique called air abrasive dentistry. In this procedure, the dental drill normally used to remove decayed tooth material is supplemented or replaced by a high velocity air stream containing particles which abrade away the decayed tooth portions. In such procedures, an inherent problem is that some of the abrasive particles will ricochet off the tooth and impact the mirror surface with sufficient velocity to etch and damage it. Dental mirrors used in such procedures can have a very short lifetime, depending on the location of the cavity, and can become unusable within a few seconds.

For these and other reasons, disposable dental mirrors have become popular in recent years. Disposable dental mirrors may be discarded after use so sterilization is not needed and transmission of viable pathogens between patients is completely avoided. In order to be economically viable, a disposable dental mirror must be very inexpensive to manufacture.

Typically, disposable dental mirrors are similar in configuration to the conventional, non-disposable mirror described above, but are made with less expensive materials. Handles may be a plastic material which can be made in large quantities at low expense by injection molding or other modern manufacturing methods. The reflecting surface is most often provided by a glass mirror.

SUMMARY OF THE INVENTION

The present invention includes a dental mirror with a novel configuration that makes it easier and more comfortable to manipulate than prior art mirrors. It includes a handle and a head section on which is located the reflective surface. As used herein, the term dental mirror refers to the entire instrument, and the term head section refers to the flat, usually-rounded portion at the distal end of the dental mirror which includes the reflective surface. The head section may, for example, be constructed of a glass mirror either held by its edges in brackets or mounted in a receiving cavity in the head section. Alternatively, the head section may be a flat surface to which is mounted a glass mirror or other reflective surface.

In the present invention, the handle is attached to the head section by means of an s-shaped intermediate section so that the handle is offset upwardly compared with conventional dental mirrors. Additionally, concave grooves on the bottom of the handle and/or intermediate section and a finger rest on top at the distal end of the handle may be provided to further enhance the dental mirror's manipulatability.

In one embodiment, the invention includes a unitary structure made of molded plastic and comprising the handle, intermediate section, and head section with a thin plastic reflective film attached to the top surface of the head section. Selecting the proper thickness for the head section of the dental mirror is important in reducing distortion when this method of manufacture is used.

DESCRIPTION OF THE DRAWINGS

The advantages and operation of the present invention are more fully described in the following description of the preferred embodiment and by reference to the drawings, of which.

DESCRIPTION OF THE PREFERRED EMBODIMENT

Figure 1:
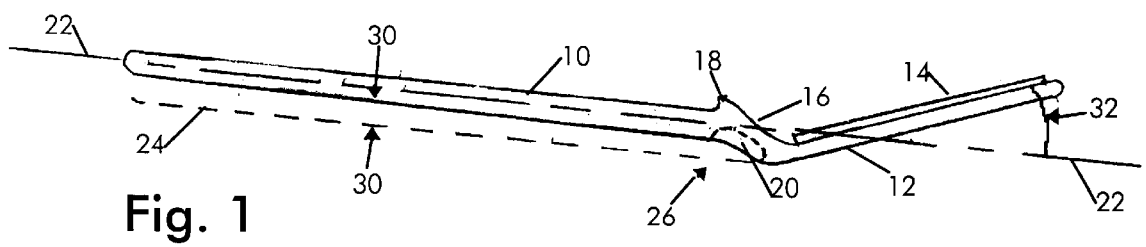
FIG. 1 is a side view of a dental mirror embodying the invention.
Figure 2:
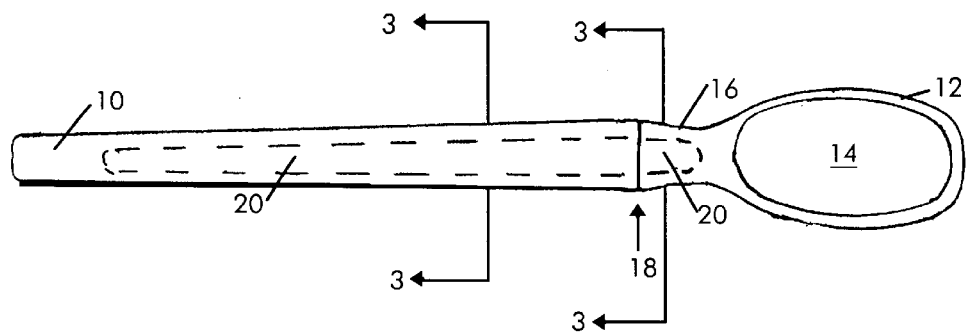
FIG. 2 is a top view of the dental mirror of FIG. 1.

FIG. 1 is a side view of a dental mirror embodying the invention, and FIG. 2 is a top view of the dental mirror. The dental mirror includes a handle 10 and a head section 12. As shown in FIGS. 1 and 2, handle 10 is preferably wider than thick to provide for easier manipulation. This is a matter of preference, however, and the present invention may be modified by providing a round, triangular, or other shape of handle.

Head section 12 is flat and has attached to the top surface a reflecting surface 14. The head section is preferably oval in shape, as shown in FIG. 2, but it may also be circular or otherwise shaped. Reflecting surface 14 is preferably formed of a thin, reflecting film that is attached to the head section by means of an adhesive. This film may be made of a thin, metallized, transparent, plastic film. In this case, the metallized layer is preferably on the bottom side so that the plastic film is on top and protects the metallization. Other types of reflecting films may be used, such as the plastic material described in U.S. Pat. No. 3,711,176. Alternatively, a conventional glass mirror may be used to provide reflective surface 14.

In the present invention the head section 12 of the dental mirror is attached to the handle by means of an intermediate section 16. Section 16 is in the form of a gooseneck or "s-shape", as shown in FIG. 1, so that the handle is offset upwardly from where conventional dental mirror handles are located. This can be seen in FIG. 1 where line 22 represents the axis of the handle and passes through the plane defined by the top surface of the head section an appreciable distance forward of its rear edge, where the right side is considered forward and the left side is considered rearward. This provides an upward offset to the handle.

Prior art dental mirrors have their handles attached at or behind the proximal, or back, edge of the head section on which the glass mirror or other reflecting surface is mounted. In other words, the axis of the dental mirror handle intersects the plane of the head section at or behind the proximal or rear edge of the reflecting surface. See, for example, U.S. Pat. Nos. 4,512,635 and 5,052,925, which show dental mirrors with the handle attached at the rear of the head section so that the handle axis intersects the head section at the proximal edge of the reflecting surface; and see U.S. Pat. Nos. 4,512,635 and Des 348,515 for dental mirrors where the handle axis intersects the plane of the reflecting surface an appreciable distance proximal or behind the location where the reflecting surface is located.

The configuration of the present invention provides several advantages over dental mirrors known heretofore. As well as serving its function as a reflecting tool, dental mirrors are frequently used by dentists to hold a patient's tongue, cheek, or other tissue away from the work area. Additionally, as well as holding tissue away, dental mirrors also sometimes serve a protective purpose. When drilling or performing other procedures on a tooth, the large flat head section of the dental mirror (as compared to the much smaller tooth surface being worked on) is placed behind the tooth to hold the cheek or tongue away, and also serves to protect the soft tissues from the drill or tool in the event it slips.

The offset provided by the s-shaped intermediate section in the present invention provides a shape that is easier for a dentist to manipulate and more comfortable for the patient. When head section 12 of the new dental mirror is holding back the cheek or tongue, the dental mirror is less prone to pull on a patient's cheek and lips due to the offset provided by intermediate section 16.

Additionally, the configuration provides greater control over the dental mirror by the dentist. When manipulating a dental mirror, a dentist will frequently hold the dental mirror with the middle finger or index finger underneath the dental mirror handle and very close to the head section. With the present invention, a dentist holding the dental mirror in this fashion will tend to locate his or her finger so that it is cradled by the concave bend 26 provided by the curve in intermediate section 16.

The manipulatability and comfort of the dental mirror can be further enhanced by adding a concave groove 20 in the bottom surface of the intermediate section. This groove is illustrated in FIG. 1. Groove 20 in the intermediate section may be extended up the handle toward the proximal end of the dental mirror to further enhance manipulatability. This is illustrated in FIG. 2 which shows groove 20 extending proximally up the underside of the handle. This groove tends to aid in keeping the dental mirror positioned on a dentist's finger when he or she is holding the dental mirror further up the handle.

Figure 3:
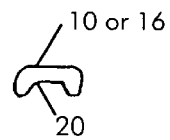
FIG. 3 is a cross-sectional view showing the shape of the concave grooves in the intermediate section and the handle.

FIG. 3 is a cross-section through the intermediate section taken at planes 3-3 in FIG. 2, and illustrates the configuration of the groove. Groove 20 aides in keeping the dental mirror from slipping sideways off of the supporting finger. Thus, the dental mirror configuration of the present invention enables a dentist's finger to be positioned underneath the intermediate section where it is secured lengthwise by the bend 26 in the intermediate section and laterally by the concave groove 20.

The manipulatability of the dental mirror can be further enhanced by adding a small upwardly projecting finger rest 18 located at or near the point where handle 10 and intermediate section 16 meet. This finger rest provides tactile feedback to a dentist as the dental mirror is moved longitudinally forward and backwards in the dentist's hand during dental procedures and reduces the tendency for the dentist's finger on top of the handle to slide off the handle down the inclined top surface of intermediate section 16. This is particularly helpful when the dental mirror is being used to push on a structure in the mouth. The proximal side of finger rest 18 is preferably perpendicular to the top surface of the handle to provide a surface which is easily engaged by a finger tip when the dental mirror is moved forward. This configuration also minimizes finger fatigue caused by tightly gripping a rotatable dental mirror handle.

The new dental mirror is preferably seven inches or less in length. The offset of the handle provided by the s-shaped intermediate section should be between one-eighth and three-eighths of an inch. The term offset as used herein means the distance between the underside of the handle 10 and a line (dashed line 24 in FIG. 1) drawn parallel to the handle and beginning at the back edge of the bottom surface of head section 12. The offset distance is shown by arrows 30 in FIG. 1. The angle 32 between the handle axis and the reflecting surface mounted of the head section is preferably between 15 and 25 degrees and more preferably about 20 degrees. The axis of the handle as that term is used herein means a line parallel with the handle and centered vertically and horizontally within the cross-sectional outline of the handle.

The described embodiment is 5.8 inches long, when viewed from the top, with a head section about 0.88 inches wide by 1.50 inches long. Groove 20 in the underside of the handle begins about one inch down from the proximal end of handle 10. The handle width goes from 0.25 inches at the proximal tip to 0.38 inches at finger rest 18. The handle thickness is 0.13 inches at the proximal tip and 0.18 inches just proximal to the finger rest 18. Finger rest 18 extends 0.07 inches above the top surface of handle 10.

The improved dental mirror of this invention may be made from many materials, including plastic, stainless steel, or other material suitable for dental instruments. The preferred method of manufacture is injection molding the dental mirror from a plastic resin. The preferred plastic resin, considering both cost and rigidity, is high impact polystyrene, although many other plastic resins may be used. Injection molding provides for rapid and inexpensive manufacture of the dental mirrors while maintaining the necessary tolerances. In particular, when the reflective surface 14 is provided by a thin reflective film applied to the top surface of the head section, it is very important that the top surface of head section 12 be kept very flat. Any curvature or imperfections in the top surface will result in distortion of the reflective surface.

In an injection-molded dental mirror, it has been discovered that the thickness of the head section 12 is very important in keeping the reflective surface flat and distortion free. If head section 12 is too thin it will tend to bend during use, providing a distorted image. There is, however, a limit on how thick the head section may be made when the dental mirror is manufactured by injection molding. During the molding process, hot plastic is forced into a mold under pressure, after which the mold is actively cooled before the individual pieces are removed from the mold. During the cooling process, the plastic material will shrink. A potential problem with injection molding the dental mirrors of the present invention is that during the cooling process, so-called "sink holes" or small pits sometimes tend to form on the top surface of head section 12 where the reflective film is attached, producing unacceptable distortions in the reflections. It has been discovered that as the thickness of head section 12 increases, the tendency to produce sink holes also increases.

Keeping the thickness of the head section within a very limited range will provide a substrate for the reflecting material thick enough that it won't bend during use while reducing or eliminating the occurrence of sink holes. The thickness of the head section is preferably between 0.070 to 0.120 inches, and more preferably between 0.078 and 0.100 inches and even more preferably between 0.082 and 0.096 inches.

Additionally, injection molded thermoplastics will tend to shrink very slightly for a significant period of time, even after coming to room temperature. If a reflective plastic film is applied to the top surface before this shrinkage has ceased, distortion will result. Thus, when the reflective surface is provided by an adhesively-attached plastic reflective film, the film should not be attached for at least 6 and preferably 24 hours after the dental mirror is removed from its mold.

There has been described a new and improved dental mirror along with a method for manufacturing the dental mirror. While the operation and advantages of the invention have been explained with reference to the exemplary embodiments described above, it should be appreciated that modifications to these embodiments will be made by those of ordinary skill in the art in applying the teachings of the invention to different situations and applications. Accordingly, the present invention should not be limited by the embodiments described above, but rather the scope of the invention should be only interpreted in accordance with the following claims.

What is claimed is:

1. A dental mirror comprising:
   a handle in the form of a elongate shaft and having a lengthwise axis that runs along the length of the handle;
   a head section having a flat top surface surrounded by a continuous edge, at least a portion of the top surface being covered by a reflective material; and
   an s-shaped intermediate section connecting the handle to the head section with an upward offset so that the axis of the handle intersects the flat top surface distally of the most proximal section of the surrounding edge, the intermediate section further including a concave groove in its underside thereby to help maintain a finger in position under the intermediate section when the mirror is being manipulated.

2. The dental mirror of claim 1 wherein the handle is wider than it is thick and includes a concave groove in its underside, extending lengthwise along the handle, which is continuous with and forms an extension to the concave groove in the intermediate section.

3. The dental mirror of claim 2 wherein the handle further includes a finger rest extending upwardly from the handle top surface where the handle meets the intermediate section.

4. The dental mirror of claim 3 wherein the reflective material further includes a thin reflective film applied to the top surface of the head section.

5. The dental mirror of claim 3 wherein the reflective material is provided by a thin, plastic, reflective film attached to the top surface of the head section by means of an adhesive.

6. The dental mirror of claim 1 wherein the reflective material includes a thin, glass mirror.

7. The dental mirror of claim 1 wherein the reflective material includes a thin reflective film applied to the top surface of the head section.

8. The dental mirror of claim 7 wherein the handle, intermediate section, and head section are formed from a unitary piece of injection-molded plastic;
   wherein the head section is in the shape of a thin, flat, blade having substantially parallel top and bottom surfaces; and
   wherein the thickness of the head section is between 0.070 and 0.120 inches.

9. The dental mirror of claim 8 wherein the thickness of the head section is between 0.078 and 0.100 inches.

10. The dental mirror of claim 9 wherein the mirror is made of polystyrene.

11. The dental mirror of claim 8 wherein the thickness of the head section is between 0.082 and 0.096 inches.

12. The dental mirror of claim 11 wherein the mirror is made of polystyrene.

13. A dental mirror comprising:
    a handle in the form of an elongate shaft and having a lengthwise axis that runs along the length of the handle;
    a head section having a flat top surface surrounded by a continuous edge, at least a portion of the top surface being covered by a reflective material; and
    an s-shaped intermediate section connecting the handle to the head section with an upward offset so that the axis of the handle intersects the flat top surface distally of the most proximal section of the surrounding edge;
    wherein the handle includes a finger rest extending upwardly from the top surface of the handle where the handle meets the intermediate section.

14. The dental mirror of claim 13 wherein the s-shaped intermediate section of the dental mirror provides an upward offset of the handle of between one-eighth and three-eights of an inch.

15. The dental mirror of claim 14 wherein the angle between the handle axis and the top surface of the head section is between 15 and 25 degrees.

16. The dental mirror of claim 15 wherein the offset is about three-sixteenth of an inch and the angle is about twenty degrees.

17. A method of manufacturing a dental mirror including the steps of:
    injection molding as a unitary piece an elongate handle section attached to a tin, flat head section having parallel top and bottom surfaces and a thickness between 0.070 and 0.120 inches; and
    applying a thin reflective film to the top surface of the head section by means of an adhesive; and
    further including the step of waiting at least 6 hours between the steps of injection molding the unitary piece and applying the reflective film.

18. The method of claim 17 further including the step of waiting at least 24 hours between the steps of injection molding the unitary piece and applying the reflective film.

19. A dental mirror comprising:
    a handle in the form of a elongate shaft having proximal and distal ends;
    a head section having a flat top surface surrounded by a continuous edge, at least a portion of the top surface being covered by a reflective material, the head section being attached to the distal end of the handle; and
    a finger rest in the form of a protuberance extending upwardly from the handle and located at the distal end of the handle.

20. The dental mirror of claim 19 wherein the proximal side of the finger rest is oriented at right angles to the handle.

21. The dental mirror of claim 20 wherein the finger rest extends upwardly approximately 0.07 inches above the handle surface.

\* \* \* \* \*